(12) United States Patent
Mintz

(10) Patent No.: US 8,653,022 B2
(45) Date of Patent: Feb. 18, 2014

(54) USE OF GHRELIN SPLICE VARIANT FOR TREATING HYPERCHOLESTEROLEMIA AND/OR HIGH CHOLESTEROL AND/OR HIGH CHOLESTEROL COMPLICATION AND/OR LIPEMIA AND/OR LIPEMIA COMPLICATION AND/OR CORONARY HEART DISEASE AND/OR WEIGHT MANAGEMENT AND/OR DIABETES AND/OR HYPERGLYCEMIA

(76) Inventor: Liat Mintz, East Brunswick, NJ (US)

(*) Notice: Subject to any disclaimer, the term of this patent is extended or adjusted under 35 U.S.C. 154(b) by 854 days.

(21) Appl. No.: 12/294,823

(22) PCT Filed: Mar. 27, 2007

(86) PCT No.: PCT/US2007/007534
§ 371 (c)(1),
(2), (4) Date: Jun. 16, 2011

(87) PCT Pub. No.: WO2007/126792
PCT Pub. Date: Nov. 8, 2007

(65) Prior Publication Data
US 2011/0245161 A1 Oct. 6, 2011

Related U.S. Application Data

(60) Provisional application No. 60/786,616, filed on Mar. 28, 2006.

(51) Int. Cl.
*A61K 38/00* (2006.01)
*A61P 3/06* (2006.01)

(52) U.S. Cl.
USPC .................................... 514/1.1; 514/7.4

(58) Field of Classification Search
None
See application file for complete search history.

(56) References Cited

U.S. PATENT DOCUMENTS

| | | | |
|---|---|---|---|
| 8,088,730 B2 * | 1/2012 | Mintz | 514/4.9 |
| 2005/0059015 A1 | 3/2005 | Mintz | |

FOREIGN PATENT DOCUMENTS

| | | |
|---|---|---|
| WO | WO03/051389 A2 | 6/2003 |
| WO | WO2005/039624 A1 | 5/2005 |
| WO | WO2007/108990 A2 | 9/2007 |

OTHER PUBLICATIONS

"Effective Health Care Program: Treating High Cholesterol, A Guide for Adults" Agency for Healthcare Research and Quality. Published Sep. 1, 2009.*

*Wyeth* v *Abbott Laboratories*. United States District Court for the District of New Jersey. 2012-1223,-1224, Jun. 26, 2013.*
Nieminen P and Mustonen AM "Effects of peripheral ghrelin on the carbohydrate and lipid metabolism of the tundra vole (*Microtus oeconomus*)" Gen and Compar Endocrin 138:182-187. Published online Jun. 26, 2004.*
Kojima M. et al., Ghrelin is a growth-hormone-releasing acylated peptide from stomach, Nature, vol. 402, pp. 656-660, Dec 9, 1999.
Neufeld, G. et al., Vascular endothelial growth factor (VEGF) and its receptors, FASEB J., vol. 13: p. 9-22, Jan. 1999.
Bednarek M et al., Function Studies on the New Growth Hormone-Releasing Peptide, Ghrelin . . . , J. Med. Chem., 43, 4370-4376, 2000.
Tschop, M. et al., Ghrelin Induces adiposity in rodents, Letters of Nature, vol. 407 p. 908-913, Oct. 19, 2000.
Hosoda, H. et al., Purification and Characterization of Rat des-Gln14-Ghrelin . . . , J. Biol. Chem., vol. 275, No. 29, Issue of Jul. 21, pp. 21995-22000 (2000).
Wren, A.M. et al., Ghrelin Causes Hyperphagia and Obesity in Rats, Diabetes, vol. 50, pp. 2540-2547, Nov. 2001.
Wren, A.M. et al., Ghrelin Enhances Appetite and Increases Food Intake in Humans, J. Clin. Endocrinol.& Metab., 86(12):5992-95, Dec. 2001.
Cummings, D.E. et al.,Plasma Ghrelin Levels after Diet-Induced Weight Loss or Gastric Bypass Surgery, N. Eng. J. Med. 346(21):1623-30 (2002).
Beaumont, N. J. et al., Ghrelin can Bind to a Species of High Density Lipoprotein Associated with Paroxonase. J.Biol.Chem : 278(11):8877-80 (2003).
Pemberton, C. et al. C-terminal pro-ghrelin peptides are present in the human circulation, Biochem. Biophys. Res. Comm., 310:567-73 (2003).
De Vriese, C. et al., Ghrelin Degradation by Serum and Tissue Homogenates . . . , Endocrinology, 145(11):4997-5005, Nov. 2004.
Gauna, C. Eet al., , Administration of Acylated Ghrelin Reduces Insulin Sensitivity . . . , J. Clin. Endocrinol. Metab., 89(10):5035-42, Oct. 2004.
Druce, M.R. et al., Subcutaneous Administration of Ghrelin . . . , Int. J. Obes. Relat. Metab. Disord. 29:1130-36 (2005).
Kojima, M. et al., Ghrelin: Structure and Function, Physiol. Rev., 85:495-522 (2005).
Zhang, J.V. et al., Obestatin, a Peptide Encoded by the Ghrelin Gene . . . , Science, vol. 310, pp. 996-999, Nov. 11, 2005.
GenBank Accession #NP-057446, Dec. 1999.
Corresponding PCT/US2007/007534 Search Report, dated Apr. 2, 2008.
Corresponding PCT/US2007/007534 Notification Concerning Transmittal of International Preliminary Report on Patentability dated Oct. 9, 2008.
Copending U.S. Appl. No. 11/716,137, filed Mar. 9, 2007.

* cited by examiner

*Primary Examiner* — Cecilia J Tsang
*Assistant Examiner* — Zachary J Miknis

(57) ABSTRACT

The present disclosure relates, in one aspect, to use of ghrelin splice variant or an analogue thereof for the preparation of a medicament for one or more of: treatment and/or prevention of hypercholesterolemia and/or high cholesterol and/or high cholesterol complication and/or lipemia and/or lipemia complication and/or CHD and/or weight management and/or diabetes and/or hyperglycemia.

17 Claims, 3 Drawing Sheets

A.

B.

USE OF GHRELIN SPLICE VARIANT FOR TREATING HYPERCHOLESTEROLEMIA AND/OR HIGH CHOLESTEROL AND/OR HIGH CHOLESTEROL COMPLICATION AND/OR LIPEMIA AND/OR LIPEMIA COMPLICATION AND/OR CORONARY HEART DISEASE AND/OR WEIGHT MANAGEMENT AND/OR DIABETES AND/OR HYPERGLYCEMIA

CROSS-REFERENCE TO RELATED APPLICATION

This application claims the benefit of U.S. Provisional Application No. 60/786,616, filed Mar. 28, 2006, incorporated herein by reference in its entirety.

FIELD OF INVENTION

The present disclosure relates to compounds for treating or preventing high cholesterol and/or lipemia and/or CHD (coronary heart disease) and/or weight management and/or diabetes and/or hyperglycemia and/or conditions related thereto.

BACKGROUND OF INVENTION

Ghrelin is a bioactive peptide that induces food intake, body weight gain, and adiposity in rodents (Tschop M. et al., Nature 407:908-13 (2000); Wren A. M. et al., Diabetes 50:2540-47 (2001)). Acute administration of ghrelin induces food intake in healthy men and women (Wren A. M. et al., J. Endocrinol. Metab. 86:5992-95 (2001); Druce M. R. et al., Int. J. Obes. Relat. Metab. Disord. 29:1130-36 (2005)).

The GHRL (ghrelin) gene encodes a variety of products resulting from alternatively spliced transcripts, various types of cleavage of the prepropeptide, and several post-translational modifications (Kojima M. & Kangawa M., Physiol. Rev. 85:495-522 (2005); Zhang J. V. et al., Science 310:996-99 (2005)). In addition, different degradation products are produced in various tissues (De Vriese C. at al., Endocrinology 145:4997-5005 (2004)). Some of these GHRL products are described herein.

Ghrelin is a 28 amino acid peptide bearing an n-octanoyl side chain on the third serine, resulting from the cleavage of signal and propeptide from the 117 amino acid preproghrelin and an acylation event. The acylated N-terminus of ghrelin is essential for the endocrine functions (Kojima M. at al., Nature 402:656-60 (1999); Bednarek M A et al., J. Med. Chem. 43:4370-76 (2000)). Des-acyl ghrelin, which lacks the endocrine functions, was shown to have an antagonistic effect to that of ghrelin on glucose output in vitro (Gauna C. at al., J. Clin. Endocrinol. Metab. 89:5035-42 (2004)). An alternatively-spliced ghrelin mRNA encodes a 116 amino acid prepropeptide that is further processed to a Des-Gln14-ghrelin and a 27 amino acid processed peptide (Hosoda H. at al., J Biol. Chem. 275:21995-22000 (2000)). Another peptide, Obestatin, is cleaved from the preproghrelin and has no sequence overlap with processed ghrelin peptide. It was shown to have some antagonistic effect to acylated ghrelin, inhibiting food intake and body weight gain (Zhang J. V. at al., Science 310:996-99 (2005)). Yet another peptide, the 66 amino acid C-terminus of the preproghrelin, may also be functional (Pemberton C. at al., Biochem. Biophys. Res. Comm. 310:567-73 (2003)). A variety of isoforms, including isoforms encoded by different splice variants, are known for other proteins, e.g. for vascular endothelial growth factor (VEGF) where different isoforms share roles as angiogenesis, while differing in some other characteristics as binding affinity (Neufeld G. et al., FASEB J. 13:9-22 1999). Thus, the variety of products of the GHRL gene may reflect a similarly complex control of the endocrine and paracrine action of the ghrelin isoforms.

Ghrelin was previously shown to specifically bind a species of high density lipoprotein associated with the plasma esterase, paraoxonase, and clusterin. An endogenous species of ghrelin was found to co-purify with high density lipoprotein during density gradient centrifugation and subsequent gel filtration. This interaction links the orexigenic peptide hormone ghrelin to lipid transport and metabolism (Beaumont J. et al., J. Biol. Chem. 11:8877-80 (2003)).

Research from experimental animals, laboratory investigations, epidemiology and genetic forms of hypercholesterolemia indicate that elevated cholesterol is a major cause of CHD (Coronary Heart Disease). The Framingham Heart Study also established that high blood cholesterol is a risk factor for CHD. Results of the Framingham study showed that the higher the cholesterol level, the greater the risk of suffering CHD. On the other end of the spectrum, CHD is uncommon at total cholesterol levels below 150 milligrams per deciliter (mg/dL). A direct link between high blood cholesterol and CHD has been confirmed by the Lipid Research Clinics-Coronary Primary Prevention Trial (1984), which showed that lowering total and LDL cholesterol levels significantly reduces CHD. A series of more recent trials of cholesterol lowering using statin drugs has demonstrated conclusively that lowering total cholesterol and LDL-cholesterol reduces the chance of suffering a heart attack, needing bypass surgery or angioplasty, and dying of CHD-related causes.

Ghrelin is synthesized in the stomach (as well as in the intestine, pituitary gland, and possibly in the hypothalamus) and activates the growth hormone secretagogue receptor. Ghrelin secretion increases with decreased food intake in animals and humans and stimulates food intake. Thus, the "drive to eat" after dieting may be partially because of ghrelin secretion. Reducing ghrelin activity may reduce the "drive to eat," and, in fact, it has been suggested that it is the reduction in ghrelin that partially accounts for the effectiveness of gastric bypass surgery (Cummings D E et al., N. Eng. J. Med. 346(21):1623-30 (2002)). Therefore, ghrelin antagonism may potentially decrease or at least blunt the increased appetite that may occur with decreased feeding and, thus, be a potential adjunctive treatment for obesity.

Obesity is the most common metabolic disease in developed nations. Despite public health education and initiatives, its prevalence continues to increase, with 30% of adults in the United States being obese and 60% of adults being overweight or obese. The World Health Organization has estimated that worldwide, over one billion adults are overweight, with at least 300 million of them being obese. The increasing prevalence of obesity among children and adolescents is also of great concern and suggests a likelihood of worsening obesity trends in future adults. Obesity leads to, or significantly increases the risk of, comorbidities involving various body systems including complications in the following systems: 1) cardiovascular [hypertension, congestive cardiomyopathy, varicosities, pulmonary embolism, coronary heart disease (CHD)], 2) neurological (stroke, idiopathic intracranial hypertension, meralgia parethetica), 3) respiratory (dyspnea, obstructive sleep apnea, hypoventilation syndrome, Pickwickian syndrome, asthma), 4) musculoskeletal (immobility, degenerative osteoarthritis, low back pain), 5) skin (striae distensae or "stretch marks," venous stasis of the lower extremities, lymphedema, cellulitis, intertrigo, carbuncles, acanthosis nigracans, skin tags), 6) gastrointestinal (GI; gastro-esophageal reflux disorder, nonalcoholic fatty liver/steatohepatitis, cholelithiasis, hernias, colon cancer), 7) genitourinary (stress incontinence, obesity-related glomerulopathy, breast and uterine cancer), 8) psychological (depression and low self-esteem, impaired quality of life), and 9) endocrine (metabolic syndrome, type 2 diabetes, dyslipidemia, hyperandrogenemia in women, polycystic ovarian syndrome, dysmenorrhea, infertility, pregnancy complications, male hypogonadism). Therefore, it has been a therapeutic and scientific goal to develop strategies to reduce the worldwide obesity epidemic to develop safe and effective antiobesity drugs, analogous to the development of treatments against hypertension, dyslipidemia, and diabetes.

SUMMARY OF THE INVENTION

One aspect is a method of treating high cholesterol levels comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid optionally being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

An additional aspect is a method for preventing high cholesterol levels comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

A further aspect is a method of treating CHD (Coronary Heart Disease) comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

An additional aspect is a method for preventing CHD (Coronary Heart Disease) comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

Another aspect is a method for treating lipemia comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

A further aspect is a method for preventing lipemia comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-

(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

Another aspect is a method for treating unwanted weight gain and maintaining the weight loss thereof comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

An additional aspect is a method for preventing weight gain comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

An additional aspect is a method of treating high cholesterol and/or lipemia and/or CHD and/or weight gain and conditions related thereto comprising administering to a mammal in need thereof a pharmaceutically acceptable amount of a secretagogue comprising (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof; wherein treatment is selected from the group consisting of prophylaxis or treatment of high cholesterol, prophylaxis or treatment of lipemia, prophylaxis or treatment of CHD, prophylaxis or treatment of conditions related to high cholesterol and/or lipemia or a combination thereof.

Another aspect is for a method for treating diabetes comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

A further aspect is for a method for treating hyperglycemia comprising administering to a mammal in need thereof a pharmaceutically acceptable amount of (a) ghrelin splice variant, preferably a ghrelin splice variant having the sequence set forth in SEQ ID NO:1, SEQ ID NO:5, SEQ ID NO:6, SEQ ID NO:7, or a fragment of 15 amino acids or more thereof; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

Other objects and advantages will become apparent to those skilled in the art upon reference to the detailed description that hereinafter follows.

BRIEF DESCRIPTION OF THE SEQUENCES

SEQ ID NO:1 represents human prepro ghrelin splice variant after the signaling sequence (GSSFLSPEHQRVQVRP- PHKAPHVVPALPLSNQLCDLEQQRHL-WASVFSQSTKDS GSDLTVSGRTWGLRVLNQLF-PPSSRERSRRSHQPSCSPEL).

SEQ ID NO:2 represents 29 amino acid human ghrelin splice variant (acylated or un-acylated) (GSSFLSPE-HQRVQVRPPHKAPHVVPALPL).

SEQ ID NO:3 represents 22 amino acid human ghrelin splice variant (acylated or un-acylated) (GSSFLSPE-HQRVQVRPPHKAPH).

SEQ ID NO:4 represents acylated 24 amino acid human ghrelin splice variant (GSSFLSPEHQRVQVRPPH-KAPHVV).

SEQ ID NO:5 represents a fragment of full-length human ghrelin splice variant (FLSPEHQRVQVRPPHKAPHV-VPALPLSNQLCDLEQQRHLWASVFSQSTKDSGSD LTVSGRTWGLRVLNQLFPPSSR-ERSRRSHQPSCSPEL).

SEQ ID NO:6 represents mouse prepro ghrelin splice variant after the signaling sequence (GSSFLSPEHQKAQVSQS-VSLSPHIYPDLCVCVRERE REPSF-PFQQRKESKKPPAK LQPRALEGWLHPEDRGQAEE-TEEELEIRVCTQAPACSYNSKGVGVWRVSHMLAF QATQGLESSTNSSTRGSESPSQEVTVSR-VAREQQTCAQKTKQIEGSQEPGSTDGY RNRRKP-CLSQDLSGLPW).

SEQ ID NO:7 represents rat prepro ghrelin splice variant after the signaling sequence (GSSFLSPEHQKAQVSL-SPQVPHLSWSVVCSFPFQQRKESKKPPA-KLQPRALEGW LHPEDRGQAEEAEEELEIRVGPRA-PAYSCNSKGFGV).

DETAILED DESCRIPTION OF THE INVENTION

Figure 1:
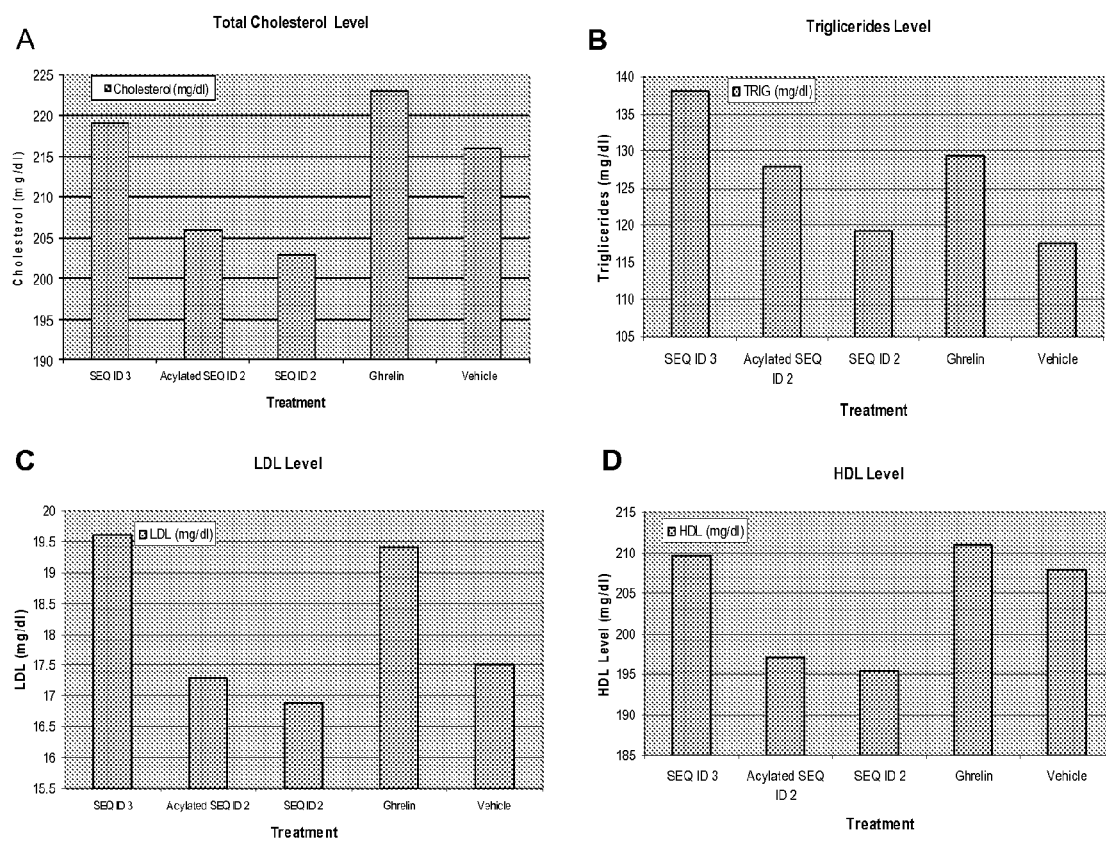
FIG. 1A is a bar graph showing serum cholesterol concentration after subcutaneous administration of acylated ghrelin splice variant (acylated SEQ ID NO:2) or un-acylated ghrelin splice variant (SEQ ID NO:2) compared to SEQ ID NO:3 and vehicle-administered controls in 129Sv mice. Reduced levels of cholesterol in the acylated ghrelin splice variant (acylated SEQ ID NO:2) and un-acylated ghrelin splice variant (SEQ ID NO:2) treated groups were observed (5% & 6%, respectively).
FIG. 1B is a bar graph showing increased levels of triglycerides in the acylated ghrelin splice variant SEQ ID NO:2 and SEQ ID NO:3 (9 and 15% respectively). The level of triglycerides in the un-acylated ghrelin splice variant SEQ ID NO:2 treated group remained unchanged.
FIG. 1C is a bar graph showing LDL levels remained unchanged in the acylated ghrelin splice variant (acylated SEQ ID NO:2) and un-acylated ghrelin splice variant (SEQ ID NO:2) treated groups.
FIG. 1D is a bar graph showing reduced levels of HDL in the acylated ghrelin splice variant (acylated SEQ ID NO:2) and un-acylated ghrelin splice variant (SEQ ID NO:2) treated groups (5% & 6%, respectively) (n=10 per group).
Figure 2:
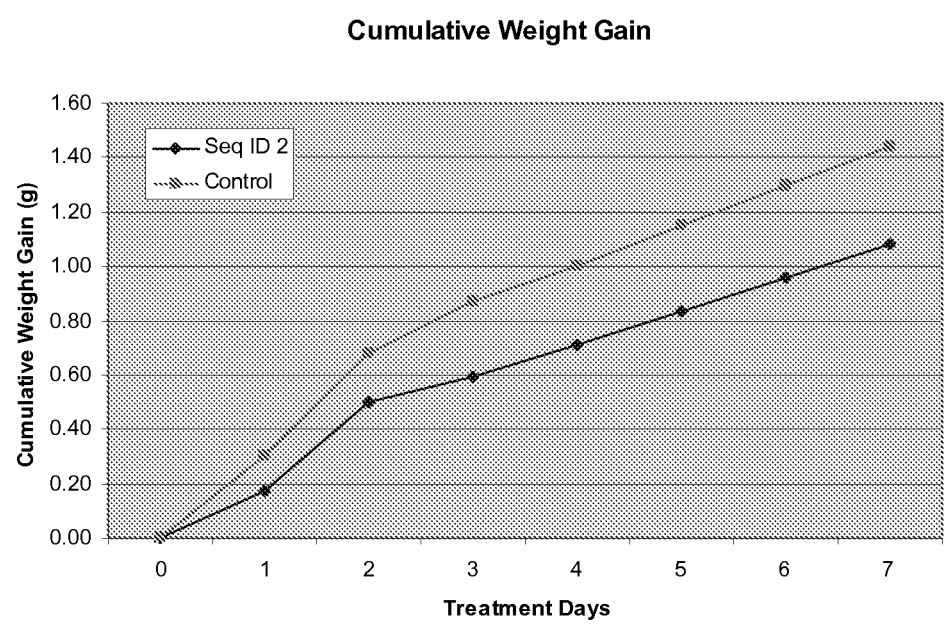
FIG. 2 is a line graph showing cumulative body weight gain of un-acylated ghrelin splice variant-treated (SEQ ID NO:2) 129Sv mice compared to vehicle-treated controls. Un-acylated ghrelin splice variant reduces body weight gain in male wild-type mice (n=8 per group). In mice treated once daily for seven days with un-acylated ghrelin splice variant (72 mg/kg, subcutaneously), cumulative weight gain of the SEQ ID NO:2 group was 25% times less than the vehicle-injected control animals.
Figure 3:
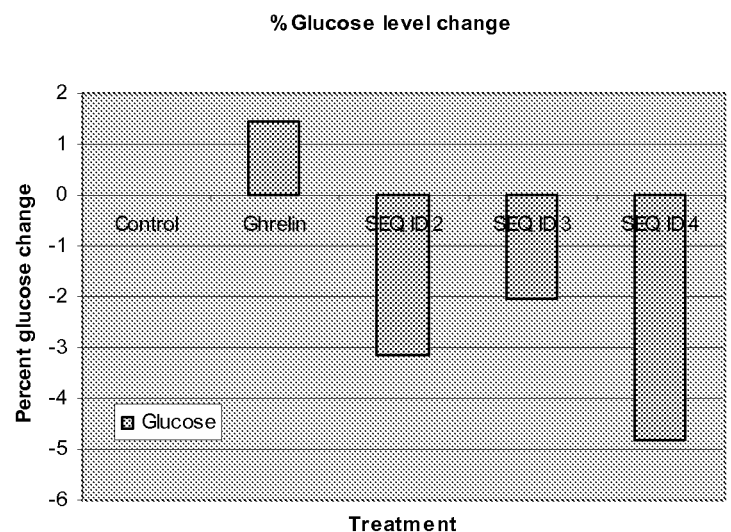
FIG. 3A is a bar graph showing percentage of plasma glucose reduction after 7 day treatment with acylated ghrelin splice variant peptides (acylated SEQ ID NO:2, SEQ ID NO:3 and SEQ ID NO:4) or ghrelin in 129Sv mice. The percent reduction is 3.2%; 2% and 4.8% respectively while treatment with ghrelin increased plasma glucose level by 1.3%.
FIG. 3B is a bar graph showing plasma glucose levels after 7 day treatment with acylated ghrelin splice variant peptides (acylated SEQ ID NO:2, SEQ ID NO:3 and SEQ ID NO:4) or ghrelin. 129 male mice were treated for seven days with 7.2 mg/kg peptide. Plasma glucose levels were measured at the end of the study.
Figure 3:
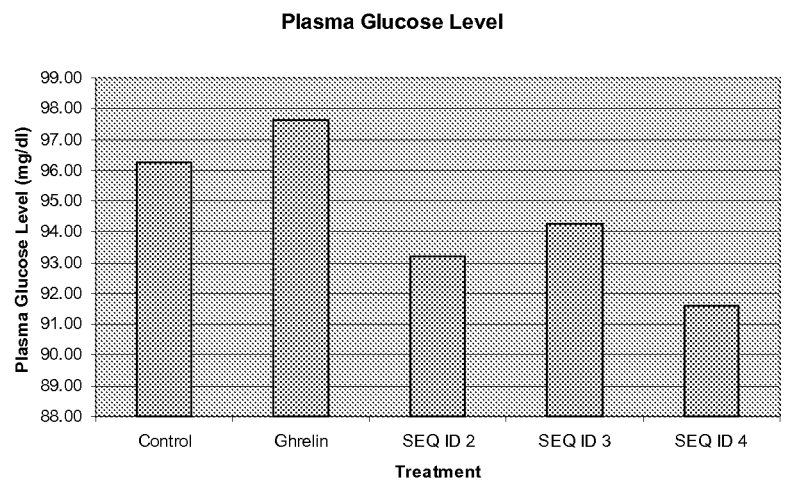

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In the context of this disclosure, a number of terms shall be utilized.

"Ghrelin" as used herein is a polypeptide having the amino acid sequence as set forth in GenBank® Accession No. NP_057446 or Swiss-Prot Identifier GHRL_HUMAN. Ghrelin preprotein has 117 amino acids. This preprotein undergoes the following post-translational processing. The signal peptide (amino acids 1-23) is removed and the remaining 94 amino acids are cleaved by a protease to provide a mature 28 amino acid ghrelin (amino acids 24-51) or a mature 27 amino acid ghrelin (amino acids 24-50) and a mature 23 amino acid obestatin (amino acids 76-98). The 27 or 28 amino acid mature ghrelin peptides can be further modified at the serine at position 26 in the preprotein by either an O-octanoyl group or an O-decanoyl group. The obestatin mature peptide can be further modified at the lysine at position 98 of the preprotein by an amide group. An additional ghrelin preprotein is known, which lacks the glutamine at position 37 of the preprotein.

"Ghrelin splice variant" is a polypeptide having the amino acid sequence as set forth in SEQ ID NO:1 or any peptide of 15 amino acids or more from SEQ ID NO:1 with or without post translational modification, or any SEQ ID NO:1 homologs as set forth in SEQ ID NO:5 or SEQ ID NO:6, and/or any peptide of 15 amino acids or more from SEQ ID NO:5 or SEQ ID NO:6 with or without post translational modification. In a preferred embodiment, the ghrelin splice variant is at least 29 amino acids in length.

"Ghrelin splice variant-like compound" as used herein refers to any compound which mimics the function of ghrelin splice variant, in particular human ghrelin splice variant, particularly in terms of the ghrelin splice variant functions leading to the desired therapeutic effects described herein, such as stimulation of appetite and/or treatment and/or prophylaxis of cachexia and is defined by the Formula I: Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% (or, in alternative embodiments, 85%, 90%, 93%, 95%, 97%, 98%, 99%, 100%) homology to SEQ ID NO:1 (see co-owned, co-pending U.S. Patent Application Ser. No. 11/716,137, entitled "Use of Ghrelin Splice Variant for Treating Cachexia and/or Anorexia and/or Anorexia-Cachexia and/or Malnutrition and/or Lipodystrophy and/or Muscle Wasting and/or Appetite-Stimulation", filed Mar. 9, 2007, incorporated herein by reference). In a preferred embodiment, the ghrelin splice variant-like compound is at least 29 amino acids in length.

Production of Ghrelin Splice Variant-Like Compounds

Ghrelin splice variant-like compounds can be produced using techniques well known in the art. For example, a polypeptide region of a ghrelin splice variant-like compound can be chemically or biochemical synthesized and modified. Techniques for chemical synthesis of polypeptides are well known in the art (see, e.g., Lee V. H. L. in "Peptide and Protein Drug Delivery", New York, N.Y., M. Dekker, 1990). Examples of techniques for biochemical synthesis involving the introduction of a nucleic acid into a cell and expression of nucleic acids are provided in Ausubel F. M. et al., "Current Protocols in Molecular Biology", John Wiley, 1987-1998, and Sambrook J. et al., "Molecular Cloning, A Laboratory Manual", 2d Edition, Cold Spring Harbor Laboratory Press, 1989, each of which is incorporated herein by reference. Another exemplary technique, described in U.S. Pat. No. 5,304,489, incorporated herein by reference, is the use of a transgenic mammals having mammary gland-targeted mutations which result in the production and secretion of synthesized ghrelin splice variant-like compound in the milk of the transgenic mammal.

Pharmaceutical Compositions

While it is possible for the compounds or salts of the present disclosure to be administered as the raw chemical, it is preferred to present them in the form of a pharmaceutical composition. Another embodiment relates to a pharmaceutical composition comprising a mixture of at least two different ghrelin splice variant-like compounds, such as a mixture of a ghrelin splice variant-like compound acylated with a $C_8$ acyl and a ghrelin splice variant-like compound acylated with a $C_{10}$ acyl. Without being bound by theory, it is believed that such a mixture will have a longer half-life in plasma.

In yet another embodiment, the pharmaceutical composition comprises acylated ghrelin splice variant-like compounds, optionally compounds having different acyl chain lengths preferably selected from the group consisting of $C_7$ acyl group, $C_9$ acyl group, and $C_{11}$ acyl group, optionally in combination with a desacylated ghrelin splice variant-like compound.

Another aspect relates to a pharmaceutical composition comprising any ghrelin splice variant-like compound as defined above or a pharmaceutically acceptable salt thereof and pharmaceutical acceptable carriers, vehicles and/or excipients; said composition further comprising transport molecules. The transport molecules are primarily added in order to increase the half-life of the acylated compound, preventing premature des-acylation, since the des-acylated ghrelin splice variant might not be active at the GHS-R 1a.

Transport molecules act by having incorporated into or anchored to it a compound disclosed herein. Any suitable transport molecule known to the skilled person may be used such as, for example, liposomes, micelles, and/or microspheres.

Conventional liposomes are typically composed of phospholipids (neutral or negatively charged) and/or cholesterol. The liposomes are vesicular structures based on lipid bilayer surrounding aqueous compartments. They can vary in their physio-chemical properties such as size, lipid composition, surface charge and number, and fluidity of the phospholipids bilayer. The most frequently used lipids for liposome formation are: 1,2-Dilauroyl-sn-Glycero-3-Phosphocholine (DLPC), Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), Dioleoyl-sn-Glycero-3-Phosphocholine (DOPC), 1,2-Dimyristoyl-sn-Glycero-3-Phosphoethanolamine (DMPE), 1,2-Dipaimitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol)] (Sodium Salt) (DMPG), 1,2-Dipalmitoyl-sn-Glycero-3-[Phospho-rac-(1-glycerol)) (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine] (Sodium Salt) (DMPS), 1,2-Dipalmitoyl-sn-Glycero-3-(Phospho-L-Serine] (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipid or modifiers of liposomes are preferred, e.g., in combination with cholesterol and/or phosphatidylcholine.

Long-circulating liposomes are characterized by their ability to extravasate at body sites where the permeability of the vascular wall is increased. A preferred way to produce long circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy (Polyethylene glycol)-2000] (Ammonium Salt), 1,2-Dipalmitoyl-sn-Glycero-3-Phosphoethanolamine-N-[Methoxy (Polyethylene glycol)-5000] (Ammonium Salt), 1,2-Dioleoyl-3-Trimethylammonium-Propane (Chloride Salt) (DOTAP).

Possible lipids applicable for liposomes are supplied by Avanti Polar Lipids, Inc., (Alabaster, Ala.). Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

A variety of methods are available for preparing liposomes, as described in, e.g., Szoka F. & Papahadjopolous D., Ann. Rev. Biophys. Bioeng. 9:467-508 (1980); U.S. Pat. Nos. 4,235,871, 4,501,728 and 4,837,028; all of which are incorporated herein by reference. Another method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution. As the concentration of a solid surfactant increases, its monolayers adsorbed at the air/water or glass/water interface become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated nonionic detergents, the polyoxyethlene moieties are oriented outward and permeated by water. This arrangement is energetically favorable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces.

The size of a micelle or its aggregation number is governed largely by geometric factors. The radius of the hydrocarbon core cannot exceed the length of the extended hydrocarbon chain of the surfactant molecule. Therefore, increasing the chain length or ascending homologous series increases the aggregation number of spherical micelles. If the surfactant concentration is increased beyond a few percent and if electrolytes are added (in the case of ionic surfactants) or the temperature is raised (in the case of nonionic surfactants), the micelles increase in size. Under these conditions, the micelles are too large to remain spherical and become ellipsoidal, cylindrical or finally lamellar in shape.

Common surfactants well known to one of skill in the art can be used in the micelles of the present disclosure. Suitable surfactants include sodium laureate, sodium oleate, sodium lauryl sulfate, octaoxyethylene glycol monododecyl ether, octoxynol 9 and PLURONIC® F-127 (BASF Corp., Florham Park, N.J.). Preferred surfactants are nonionic polyoxyethylene and polyoxypropylene detergents compatible with intravenous injection such as, TWEEN®-80, PLURONIC® F-68, n-octyl-beta-D-glucopyranoside, and the like. In addition, phospholipids, such as those described for use in the production of liposomes, may also be used for micelle formation.

In another preferred embodiment, the compounds disclosed herein are formulated as described in the literature for an administration route selected from: buccal delivery, sublingual delivery, transdermal delivery, inhalation and needle-free injection, such as using the methods developed by Powderjet.

For inhalation, the compounds disclosed herein can be formulated using methods known to those skilled in the art, for example an aerosol, dry powder or solubilized such as in microdroplets, preferably in a device intended for such delivery (such as commercially available from Aradigm Corp. (Hayward, Calif.), Alkermes, Inc. (Cambridge, Mass.), or Nektar Therapeutics (San Carlos, Calif.)).

Administration

Suitable dosing regimens for the various compounds and methods of the present disclosure are preferably determined taking into account factors well known in the art including, e.g., type of subject being dosed; age, weight, sex and medical condition of the subject; the route of administration; the renal and hepatic function of the subject; the desired effect; and the particular compound employed. Preferably, the composition will comprise about 0.5% to 75% by weight of a secretagogue disclosed herein, with the remainder consisting of suitable pharmaceutical excipients.

Optimal precision in achieving concentrations of drug within the range that yields efficacy without toxicity requires a regimen based on the kinetics of the drug's availability to target sites. This involves a consideration of the distribution, equilibrium, and elimination of a drug.

As described above, in one aspect, the ghrelin splice variant or a ghrelin splice variant-like compound is administered subcutaneously.

In another aspect, the ghrelin splice variant or a ghrelin splice variant-like compound is administered as a premeal bolus, wherein the administration form may be any suitable parenteral form. In a preferred embodiment, the ghrelin splice variant or a ghrelin splice variant-like compound is administered subcutaneously in a premeal bolus.

The ghrelin splice variant or a ghrelin splice variant-like compound can also be administered during a meal as a bolus. The mode of administration during a meal includes subcutaneous administration, such as a subcutaneously administered bolus.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Other suitable administration forms include suppositories, sprays, ointments, creams, gels, inhalants, dermal patches, implants, pills, tablets, lozenges and capsules.

A typical dosage is in a concentration equivalent to from 10 ng to 10 mg ghrelin splice variant per kg bodyweight. The concentrations and amounts herein are given in equivalents of amount ghrelin splice variant, wherein the ghrelin splice variant is a 29 amino acid human ghrelin splice variant (SEQ ID NO:2) and/or a 22 amino acid human ghrelin splice variant (SEQ ID NO:3) and/or a 24 amino acid human ghrelin splice variant (SEQ ID NO:4). Equivalents may be tested as described in the section entitled "Functionality", above.

In a preferred embodiment, the medicament is administered in a concentration equivalent to from 0.1 µg to 1 mg ghrelin splice variant per kg bodyweight, such as from 0.5 µg to 0.5 mg ghrelin splice variant per kg bodyweight, such as from 1.0 µg to 0.1 mg ghrelin splice variant per kg bodyweight, such as from 1.0 µg to 50 µg ghrelin splice variant per kg bodyweight, such as from 1.0 µg to 10 µg ghrelin splice variant per kg bodyweight.

As described above, the ghrelin splice variant or a ghrelin splice variant-like compound is preferably administered as a bolus. Accordingly, in one embodiment the medicament is administered as a bolus prior to a meal, said bolus comprising an amount of the ghrelin splice variant or ghrelin splice variant-like compound or a salt thereof equivalent to from 0.3 µg to 600 mg ghrelin splice variant. More preferably, the medicament is administered as a bolus prior to a meal, said bolus comprising an amount of the ghrelin splice variant or ghrelin splice variant-like compound or a salt thereof equivalent to from 2.0 µg to 200 mg ghrelin splice variant, such as from 5.0 µg to 100 mg ghrelin splice variant, such as from 10 µg to 50 mg ghrelin splice variant, such as from 10 µg to 5 mg ghrelin splice variant, such as from 10 µg to 1.0 mg ghrelin splice variant.

It should be noted that the normal ghrelin splice variant-like response which occurs before a meal is a short-lived surge in plasma concentrations of ghrelin splice variant and that, due to the relatively short half life of the peptide, an intravenous injection of ghrelin splice variant will ensure that a similar short-lived peak on ghrelin splice variant concentrations can be obtained. The administration route must ensure that the non-degraded, bioactive form of the peptide will be the dominating form in the circulation, which will reach and stimulate the ghrelin splice variant receptors.

Thus, in order to obtain the maximum effect of the medicament, it is preferably administered from one to three times daily, each administration being within 45 minutes of a meal, such as within 30 minutes of a meal, such as within 25 minutes of a meal, such as within 20 minutes of a meal, such as within 15 minutes of a meal, such as within 10 minutes of a meal, such as within 5 minutes of a meal. More preferably, the medicament is administered prior to each main meal, such as administered three times daily.

Compounds disclosed herein may also be formulated for nasal administration. The solutions or suspensions are applied directly to the nasal cavity by conventional means, for example with a dropper, pipette or spray. The compositions may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds disclosed herein may be formulated for aerosol administration, particularly to the respiratory tract and including intranasal administration. The compound will generally have a small particle size, for example of the order of 5 microns or less. Such a particle size may be obtained by means known in the art, for example by micronization. The active ingredient is provided in a pressurized pack with a suitable propellant such as a hydrofluoroalkane (HFA) for example hydrofluoroalkane-134a and hydrofluoroalkane-227, carbon dioxide or other suitable gas. The aerosol may conveniently also contain a surfactant such as lecithin. The dose of drug may be controlled by a metered valve. Alternatively, the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of, e.g., gelatin or blister packs from which the powder may be administered by means of an inhaler.

Compositions administered by aerosols may be prepared, for example, as solutions in saline, employing benzyl alcohol or other suitable preservatives, absorption promoters to enhance bioavailability, employing fluorocarbons, and/or employing other solubilizing or dispersing agents.

Compounds disclosed herein may also be formulated for administration by injection pen in a similar way as for cartridged growth hormone (GH) or Insulin. The cartridge contains compounds disclosed herein in solvents. The pen, which is basically a needle, syringe and vial in one piece, is operated by a turning movement and allows different doses to be administrated. This device offers simplicity, convenience, and enhanced safety features for compounds delivery. It provides a simple device design, few administration steps and one-step dial-back dose knob. Such injection pen can be obtained by means known in art. For example, several manufacturers offer drug developers injection pens to be used with the drug developers compounds (BD—Medical-Pharmaceutical Systems, Inc.; Owen Mumford Inc. etc.).

Compositions for Oral Administration

Those compositions capable of remaining biologically active in an individual after oral administration (such as, e.g., small molecules and short peptides) can be formulated in a wide range of oral administration dosage forms. The pharmaceutical compositions and dosage forms may comprise the compounds disclosed herein or their pharmaceutically acceptable salt or crystal forms thereof as the active component.

The pharmaceutical acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

For oral administration, such excipients include, e.g., pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include a composition comprising an active compound disclosed herein with encapsulating material as carrier providing a capsule in which the active component, with or without carriers, is surrounded by a carrier, which is in association with it. Similarly, cachets and lozenges are included.

Tablets, powders, capsules, pills, cachets, and lozenges can be as solid forms suitable for oral administration.

Drops may comprise sterile or nonsterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Compositions for Parenteral Administration

The compounds disclosed herein may be formulated for parenteral administration (e.g., by injection, for example bolus injection or continuous infusion) and may be presented in unit dose form in ampules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water. Aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions of ghrelin splice variant or a ghrelin splice variant-like compound or pharmaceutical acceptable salt thereof (and for example antigenic epitopes and protease inhibitors) can be prepared in water or saline, and optionally mixed with a nontoxic surfactant. Compositions for intravenous or intraarterial administration may include sterile aqueous solutions that may also contain buffers, liposomes, diluents and other suitable additives.

Oils useful in parenteral compositions include petroleum, animal, vegetable, or synthetic oils. Specific examples of oils useful in such compositions include peanut, soybean, sesame, cottonseed, corn, olive, petrolatum, and mineral. Suitable fatty acids for use in parenteral compositions include oleic acid, stearic acid, and isostearic acid. Ethyl oleate and isopropyl myristate are examples of suitable fatty acid esters.

Suitable soaps for use in parenteral compositions include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates; (c) nonionic detergents such as, for example, fatty amine oxides, fatty acid alkanolamides, and polyoxyethylenepolypropylene copolymers; (d) amphoteric detergents such as, for example, alkyl-beta-aminopropionates, and 2-alkyl-imidazoline quaternary ammonium salts; and (e) mixtures thereof.

The parenteral compositions typically will contain from about 0.5 to about 25% by weight of the active ingredient in solution. Preservatives and buffers may be used.

In order to minimize or eliminate irritation at the site of injection, such compositions may contain one or more nonionic surfactants having a hydrophile-lipophile balance (HLB) of from about 12 to about 17. The quantity of surfactant in such compositions will typically range from about 5 to about 15% by weight. Suitable surfactants include polyethylene sorbitan fatty acid esters, such as sorbitan moriooleate and the high molecular weight adducts of ethylene oxide with a hydrophobic base, formed by the condensation of propylene oxide with propylene glycol. The parenteral compositions can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating ghrelin splice variant or a ghrelin splice variant-like compound or pharmaceutical acceptable salt thereof in the required amount in the appropriate solvent with various of the other ingredients enumerated above, as required, followed by, e.g., filter sterilization.

Compositions for Topical Administration

The compounds disclosed herein can also be delivered topically. Regions for topical administration include the skin surface and also mucous membrane tissues of the rectum, nose, mouth, and throat. Compositions for topical administration via the skin and mucous membranes should not give rise to signs of irritation, such as swelling or redness.

The topical composition may include a pharmaceutical acceptable carrier adapted fortopical administration. Thus, the composition may take the form of, for example, a suspension, solution, ointment, lotion, cream, foam, aerosol, spray, suppository, implant, inhalant, tablet, capsule, dry powder, syrup, balm or lozenge. Methods for preparing such compositions are well known in the pharmaceutical industry.

The compounds disclosed herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Compositions suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present disclosure are semi-solid compositions for external application comprising the active ingredient. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives; or a fatty acid such as steric or oleic acid together with an alcohol such as propylene glycol or a macrogel. The composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present disclosure include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

The compounds described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the active compound to a patient's skin for an extended period of time. Transdermal patches have the added advantage of providing controlled delivery of a compound complex to the body (see Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987)). Such dosage forms can be made by dissolving, dispersing, or otherwise incorporating a compound disclosed herein in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

A variety of types of transdermal patches will find use in the methods described herein. For example, a simple adhesive patch can be prepared from a backing material and an acrylate adhesive. The active compound and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver a compound disclosed herein. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

A liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system (See U.S. Pat. Nos. 4,816,258; 4,927,408; 4,904,475; 4,588,580, 4,788,062; and the like, all of which are incorporated herein by reference). The rate of drug delivery will be dependent, in part, upon the nature of the membrane. For example, the rate of drug delivery across membranes within the body is generally higher than across dermal barriers. The rate at which the active compound is delivered from the device to the membrane is most advantageously controlled by the use of rate-limiting membranes which are placed between the reservoir and the skin. Assuming that the skin is sufficiently permeable to the active compound (i.e., absorption through the skin is greater than the rate of passage through the membrane), the membrane will serve to control the dosage rate experienced by the patient.

Suitable permeable membrane materials may be selected based on the desired degree of permeability, the nature of the active compound, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions disclosed herein may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

Compositions for Administration as Suppositories

The compounds disclosed herein may be formulated for administration as suppositories. A typical suppository is produced by providing a low melting wax, such as a mixture of fatty acid glycerides or cocoa butter, that is first melted and the active component is dispersed homogeneously therein, for example, by stirring. The molten homogeneous mixture is then poured into convenient sized molds, allowed to cool, and to solidify.

The active compound may be formulated into a suppository comprising, for example, about 0.5% to about 50% of a compound disclosed herein, disposed in a polyethylene glycol (PEG) carrier (e.g., PEG 1000 [96%] and PEG 4000 [4%]).

Formulation

A preferred aspect contemplates pharmaceutical compositions useful for practicing the therapeutic methods described herein. Pharmaceutical compositions can contain a physiologically tolerable carrier together with at least one species of a secretagogue, such as ghrelin splice variant or a ghrelin splice variant-like compound as described herein, dissolved or dispersed therein as an active ingredient. In a preferred embodiment, the pharmaceutical composition is not immunogenic when administered to a human individual for therapeutic purposes, unless that purpose is to induce an immune response.

One aspect relates to a pharmaceutical composition comprising at least one ghrelin splice variant or a ghrelin splice variant-like compound as defined above in Formula I. In a preferred embodiment, the pharmaceutical composition comprises at least two different ghrelin splice variant-like compounds as defined above in Formula I in order to increase the effect of the treatment. The difference may for example be compounds having different acylations as discussed above.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically, such compositions are prepared as sterile injectables either as liquid solutions or suspensions, aqueous or non-aqueous; however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. It is preferred that the formulation has a pH within the range of 3.5-8, such as in the range 4.5-7.5, such as in the range 5.5-7, such as in the range 6-7.5, most preferably around 7.3. However, as is understood by one skilled in the art, the pH range may be adjusted according to the individual treated and the administration procedure. For example, ghrelin splice variant and ghrelin splice variant homologs may be easily stabilized at a lower pH; so, in another preferred embodiment, the formulation has a pH within the range 3.5-7, such as 4-6, such as 5-6, such as 5.3-5.7, such as 5.5.

Pharmaceutical compositions disclosed herein can include pharmaceutically acceptable salts of the compounds therein. These salts will be ones which are acceptable in their application to a pharmaceutical use, meaning that the salt will retain the biological activity of the parent compound and the salt will not have untoward or deleterious effects in its application and use in treating diseases.

Pharmaceutically acceptable salts are prepared in a standard manner. If the parent compound is a base, it is treated with an excess of an organic or inorganic acid in a suitable solvent. If the parent compound is an acid, it is treated with an inorganic or organic base in a suitable solvent.

The compounds disclosed herein may be administered in the form of an alkali metal or earth alkali metal salt thereof, concurrently, simultaneously, or together with a pharmaceutically acceptable carrier or diluent, especially and preferably in the form of a pharmaceutical composition thereof, whether by, e.g., oral, rectal, or parenteral (including subcutaneous) route, in an effective amount.

Examples of pharmaceutical acceptable acid addition salts for use in the present inventive pharmaceutical composition include those derived from mineral acids, such as, e.g., hydrochloric, hydrobromic, phosphoric, metaphosphoric, nitric and sulfuric acids, and organic acids, such as, e.g., tartaric, acetic, citric, malic, lactic, fumaric, benzoic, glycolic, gluconic, succinic, p-toluenesulphonic, and arylsulphonic acids.

Other suitable pharmaceutically acceptable salts include the acid addition salts (formed with the free amino groups of the polypeptide). Other examples of salts include pharmaceutically acceptable acid addition salts, pharmaceutically acceptable metal salts, ammonium salts and alkylated ammonium salts. Acid addition salts include salts of inorganic acids as well as organic acids. Representative examples of suitable inorganic acids include hydrochloric, hydrobromic, hydriodic, phosphoric, sulfuric and nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, ethylenediaminetetraacetic (EDTA), p-aminobenzoic, glutamic, benzenesulfonic, and p-toluenesulfonic acids and the like. Further examples of pharmaceutically acceptable inorganic or organic acid addition salts include the pharmaceutical acceptable salts listed in Berge S. M. et al., J. Pharm. Sci. 66:1-19 (1977), which is incorporated herein by reference. Examples of metal salts include lithium, sodium, potassium and magnesium salts and the like.

Examples of ammonium and alkylated ammonium salts include ammonium, methylammonium, dimethylammonium, trimethylammonium, ethylammonium, hydroxyethylammonium, diethylammonium, butylammonium and tetramethylammonium salts and the like.

Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Also included within the scope of compounds or pharmaceutical acceptable acid addition salts thereof in the context of the present disclosure are any hydrates (hydrated forms) thereof.

For parenteral administration, solutions of the present compounds in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

The pharmaceutical compositions formed by combining the compounds disclosed herein and the pharmaceutical acceptable carriers are then readily administered in a variety of dosage forms suitable for the disclosed routes of administration. The formulations may conveniently be presented in unit dosage form by methods known in the art of pharmacy.

In a preferred embodiment, the formulation comprises the ghrelin splice variant or ghrelin splice variant-like compound or a salt thereof as a lyophilisate, and the formulation further comprises a solvent, said lyophilisate and said solvent being in separate compartments until administration. In another embodiment, the formulation is a solution of the ghrelin splice variant or ghrelin splice variant-like compound or a salt thereof. In either embodiment, the solvent may be any suitable solvent, such as those described herein, and preferably the solvent is saline.

Another aspect relates to a method for preparing a medicament or pharmaceutical composition comprising a compound disclosed herein, the method comprising admixing at least one ghrelin splice variant-like compound, as defined above in Formula I, with a physiologically acceptable carrier. A further aspect relates to a pharmaceutical composition comprising, as an active ingredient, a compound as defined above in Formula I or a pharmaceutically acceptable salt thereof together with a pharmaceutically-acceptable carrier. Accordingly, the formulation may further include the transport molecules as described above.

Combination Treatments

In a further aspect, the present compounds may be administered in combination with additional pharmacologically-active substances or other pharmacologically-active material and/or may be administered in combination with another therapeutic method. By the phrase "in combination with another substance(s) and/or therapeutic method(s)" is meant herein that said another substance(s) and/or therapeutic method(s) is administered to the individual thus treated before, during (including concurrently with) and/or after treatment of an individual with a secretagogue. In all cases of combination treatment described herein, the combination may be in the form of kit-in-part systems, wherein the combined active substances may be used for simultaneous, sequential or separate administration. In all cases, it is preferred that any of the herein-mentioned medicaments are administered in pharmaceutically effective amounts, i.e. an administration involving a total amount of each active component of the medicament or pharmaceutical composition or method that is sufficient to show a meaningful patient benefit.

EXAMPLES

The present disclosure is further defined in the following Examples. It should be understood that these Examples, while indicating preferred embodiments, are given by way of illustration only. From the above discussion and these Examples, one skilled in the art can ascertain the preferred features of this disclosure, and without departing from the spirit and scope thereof, can make various changes and modifications to adapt it to various uses and conditions.

Example 1

Synthetic Production of Ghrelin Splice Variant-Like Compound

Amino acid derivatives and synthesis reagents can be obtained from commercial sources. Peptide chain extension can be performed using APPLIED BIOSYSTEMS®433A synthesizer produced by Perkin Elmer, and a protected peptide derivative-resin can be constructed by the Boc or Fmoc method. The protected peptide resin obtained by the Boc method is deprotected with anhydrous hydrogen fluoride (HF) in the presence of p-cresol thereby releasing the peptide, which is then purified. The protected peptide resin obtained by the Fmoc method is deprotected with trifluoroacetic acid (TFA) or dilute TFA containing various scavengers, and the released peptide is purified. Purification is performed in reversed phase HPLC on a C4 or C18 column. The purity of the purified product can be confirmed by reverse phase HPLC, and its structure can be confirmed by amino acid composition analysis and mass spectrometry.

Peptides disclosed herein can be produced by a conventional peptide synthesis method. Specifically, synthesis of acylated or alkylated peptides is exemplified below.

Abbreviations: "HMP resin" means 4-hydroxymethylphenoxymethyl resin; "Fmoc amide resin" means 4-(2',4'-dimethoxyphenyl-Fmoc-aminomethyl) phenoxyacetamido-ethyl resin; "PAM resin" means phenylacetoamidomethyl resin; "HBTU" means 2-(1H-benzotriazole-1-yl)-1,1,3,3-tetramethyluronium hexafluorophosphate; "TBTU" means 2-(1H-benzotriazole-1-yl)-1,1,3,3-tetramethyluronium tetrafluoroborate; "HOBt" means 1-hydroxybenzotriazole; "DCC" means dicyclohexylcarbodiimide; "DIPCI" means diisopropylcarbodiimide; "TFA" means trifluoroacetic acid; "DIPEA" means diisopropylethylamine; "TIPS" means triisopropylsilane; "Fmoc" means fluorenylmethoxycarbonyl; "Boc" means t-butyloxycarbonyl; "Trt" means trityl; "Bu" means t-butyl; "Pmc" means 2,2,5,7,8-pentamethylchroman-6-sulfonyl; "Prl" means propionyl; "PhPrl" means phenylpropionyl; "Bzl" means benzyl; "Bom" means benzyloxymethyl; "Tos" means toluenesulfonyl; "Cl-Z" means 2-chlorobenzyloxycarbonyl; "Pis" means 2-phenylisopropyl; "Mtt" means 4-methyltrityl; "DMF" means N,N-dimethylformamide; "NMP" means N-methylpyrrolidone; "DMAP" means 4-dimethylaminopyridine; "HOSu" means N-hydroxysuccinimide; "Adod" means 2-aminododecanoic acid; "Aib" means 2-aminoisobutylic acid; "Ape" means 5-aminopentanoic acid; "Cha" means cyclohexylalanine; "Dap" means 2,3-diaminopropionic acid; "Nal" means naphtylalanine; "Nle" means norleucine.

Protecting amino acids which can be used in synthesis Fmoc method: Boc-Gly, Fmoc-Gly, Fmoc-Ser (Bu), Fmoc- Ser (Trt), Fmoc-Glu (OBu), Fmoc-His (Boc), Fmoc-Gln (Trt), Fmoc-Arg (Pmc), Fmoc-Lys (Boc), Fmoc-Pro, Fmoc-Leu, Fmoc-Ala, Fmoc-Val, Fmoc-Phe, Fmoc-Phe, Fmoc-Ser (n-$C_8H_{17}$), Fmoc-Ser (n-$C_8H_{17}$), Fmoc-Cys (n-$C_3H_{17}$), Fmoc-Asp (OPis), Fmoc-Ser (Bzl), Fmoc-Cys (Trt), Fmoc-Dap (Octanoyl), Fmoc-2-Nal, Fmoc-2-Nal, Fmoc-Nle, Fmoc-Lys (Mtt), Fmoc-Aib-OH, Fmoc-Asp (O-$C_7$-$H_{15}$). Boc method: Boc-Gly, Boc-Ser (Bzl), Boc-Ser (Ac), Boc-Ser (Prl), Boc-Glu (OBzl), Boc-His (Bom), Boc-Gin, Boc-Arg (Tos), Boc-Lys (Cl-Z), Boc-Pro, Boc-Leu, Boc-Ala, Boc-Val, Boc-Phe, Boc-Cys (n-$C_8H_{17}$), Boc-Ape, Boc-Ser (n-$C_8H_{17}$)

Units used:
(a) Analytical HPLC system Unit: Shimadzu LC-10A System; Column: YMC PROTEIN-RP (4.6 mm×150 mm); Column temperature: 40° C.; Eluent: A linear gradient of from 0 to 50% acetonitrile for 20 minutes in 0.1% trifluoroacetic acid; Flow rate: 1 mL/min; Detection: UV (210 nm); Injection volume: 10 to 100 mu I.
(b) Preparative HPLC system Unit: Waters 600 Multisolvent Delivery System; Columns: YMC-Pack-ODS-A (5 mu m, 20 mm×250 mm) YMC-Pack-PROTEIN-RP (5 mu m, C4, 10 mm×250 mm) YMC-Pack PROTEIN-RP (5 mu m, C4, 20 mm×250 mm) YMC PROTEIN-RP (4.6 mm×150 mm); Eluent: A suitable linear gradient of acetonitrile concentration in 0.1% trifluoroacetic acid; Flow rate: 10 mL/min. (for columns of an inner diameter of 20 mm), 3 mL/min. (for the column of an inner diameter of 10 mm), 1 mL/min. (for the column of an inner diameter of 4.6 mm); Detection: 210 nm, 260 nm; Injection: 10 to 2000 mu I (2000 mu I or more was injected via a pump)
(c) Mass spectrometer Unit: Finnigan MAT TSQ700; Ion source: ESI; Detection ion mode: Positive Spray; Voltage: 4.5 kV; Capillary temperature: 250° C.; Mobile phase: A mixture of 0.2% acetic acid and methanol (1:1); Flow rate: 0.2 mL/min; Scan range: m/z 300 to 1,500
(d) Analysis of amino acid sequence Unit: APPLIED BIOSYSTEM®477A, 492 model sequencer manufactured by Perkin Elmer
(e) Analysis of amino acid composition Unit: L-8500 model amino acid analyzer manufactured by Hitachi, Co., Ltd.; Sample: Unless otherwise specified, the sample is hydrolyzed with 6 M HCl at 110° C. for 24 hours in a sealed tube.

Example of Synthesis of a Derivative Having Acyl Serine (Fmoc Method, Carboxyl-Terminal Amide Derivatives) Ghrelin Splice Variant GSS (CO-$C_7H_{15}$) FLSPEHQRVQVRPPHKAPH Fmoc-His (Pmc)-HMP-resin (403 mg, 0.25 mmol, ABI Co., Ltd.) is treated with 20% piperazine for 20 minutes and subjected repeatedly to introduction of Fmoc-amino acid by HBTU/HOBt and elimination of Fmoc by piperazine sequentially to construct Fmoc-Ser (Bu)-Ser (Trt)-Phe-Leu-Ser (tBu)-Pro-Glu (OBu)-His (Boc)-Gln (Trt)-Arg (Pmc)-Val-Gln-Val (Trt)-Arg (Pmc)-Pro-Pro-His (Boc)-Lys (Boc)-Ala (Boc)-Pro (Boc)-Pro-His (Pmc)-resin. After Boc-Gly is finally introduced by DCC/HOBt, the resulting protected peptide resin (1.3 g) is treated with 1% TFA-5% TIPS-methylene chloride solution (15 mL) for 30 minutes.

The peptide resin is filtrated, washed several times with methylene chloride (30 mL), and washed with 5% DI EA (10 mL) and then with methylene chloride (30 mL). The resulting de-Trt peptide resin (about 1.3 g) is swollen with NMP (10 mL), and octanoic acid (144.2 mg, 1.0 mmol) and DIPCI (126.2 mg, 1.0 mmol) are added thereto in the presence of DMAP (61.1 mg, 0.5 mmol) and allowed to react for 8 hours. The resin is recovered by filtration and washed with NMP and then with methylene chloride, followed by drying under vacuum to give about 1.2 g protected peptide resin wherein the side chain of third serine is octanoylated. To this product is added a de-protecting reagent (10 mL) consisting of 88% TFA-5% phenol-2% TIPS-5% $H_2O$, and the mixture is stirred at room temperature for 2 hours. The resin is removed by filtration, and the filtrate is concentrated followed by adding ether to the resulting residues to form precipitates. The precipitates are recovered by filtration and dried to give about 550 mg crude peptide. 200 mg of this product is dissolved in 10 mL water and applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions are collected and lyophilized to give about 120 mg of the desired product.

Example of Synthesis of a Derivative Having Acyl Serine (Fmoc Method, Carboxyl-Terminal Amide Compounds) Ghrelin Splice Variant (1-22)-$NH_2$ GSS (CO-$C_7H_{15}$) FLSPEHQRVQVRPPHKAPH-$NH_2$ Fmoc-amide-resin (403 mg, 0.25 mmol, ABI Co., Ltd.) is treated with 20% piperazine for 20 minutes and subjected repeatedly to introduction of Fmoc-amino acid by HBTU/HOBt and elimination of Fmoc by piperazine sequentially to construct Fmoc-Ser (Bu)-Ser (Trt)-Phe-Leu-Ser (Bu)-Pro-Glu (OBu)-His (Boc)-Gln (Trt)-Arg (Pmc)-Val-Gln-Val (Trt)-Arg (Pmc)-Pro-Pro-His (Boc)-Lys (Boc)-Ala (Boc)-Pro (Boc)-Pro-His (Boc)-resin. After Boc-Gly is finally introduced by DCC/HOBt, the resulting protected peptide resin (about 550 mg) is treated with 1% TFA-5% TIPS-methylene chloride solution (10 mL) for 30 minutes. The peptide resin is recovered by filtration, washed several times with methylene chloride (30 mL), and washed with 5% DIEA (10 mL) and then with methylene chloride (30 mL). The resulting de-Trt peptide resin (about 750 mg) is swollen with NMP (10 mL), and octanoic acid (1442 mg, 1.0 mmol) and DIPCI (126.2 mg, 1 mmol) are added thereto in the presence of DMAP (61.1 mg, 0.5 mmol) and allowed to react for 4 hours. The resin is recovered by filtration and washed with NMP and then with methylene chloride, followed by drying under vacuum to give about 800 mg protected peptide resin wherein the side chain of third serine is octanoylated. TFA (10 mL) is added to this product and stirred at room temperature for 30 minutes. The resin is removed by filtration, and the filtrate is then concentrated followed by adding ether to the resulting residues to form precipitates. The precipitates are recovered by filtration and dried to give about 250 mg crude peptide. About 200 mg of this product is dissolved in 10 mL of 30% aqueous acetic acid and applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions are collected and then lyophilized to give about 150 mg of the desired product.

Example of Synthesis of a Derivative Having Acyl Serine (Boc Method) [Ser3 (Propionyl)]-Ghrelin Splice Variant (1-22)

GSS (CO-$CH_2CH_3$) FLSPEHQRVQVRPPHKAPH protected ghrelin splice variant resin (4-22) is constructed from Boc-His (Tos)-Pam resin (0.75 g, 0.5 mmol) by Boc chemistry, and Boc-Ser (CO-$CH_2CH_3$)-OH, Boc-Ser (Bzl)-OH and Boc-Gly-OH are condensed with a half (1.4 g) of the resin. The resulting resin, 1.5 g, is then treated with a mixture of HF and p-cresol (8.5 mL:1.5 mL) at 0° C. for 1 hour, and the HF is evaporated. Ether is added to the residues, whereby 671 mg crude peptide is obtained. This sample is then dissolved in 50% acetic acid (AcOH) and applied to a preparative column YMC-Pack-ODS-A (5 mu m, 20 mm×250 mm) and eluted at a rate of 10 mL/min by a gradient of from 0 to 95% acetonitrile concentration in 0.1% TFA solution for 75 minutes. Those fractions containing the desired product are lyophilized to give approximately 135.8 mg crude peptide. A part (0.5 mg) of this product is applied to YMC-A-302 column (C18, 4.6 mm×150 mm) and eluted at a flow rate of 1 mL/min. by a gradient of from 15 to 19% concentration acetonitrile. This purification procedure is then repeated and the desired fractions are combined to give approximately 0.41 mg of the desired product.

Other compounds according to the present disclosure can be produced likewise. Acylated and un-acylated SEQ ID NO:2, acylated and un-acylated SEQ ID NO:3 and acylated SEQ ID NO:4 were produced synthetically using the above described method.

Example 2

Efficacy of Subcutaneous Administration of Acylated and Un-Acylated Ghrelin Splice Variant on Weight Gain, Lowering Plasma Glucose Level, Lowering Cholesterol and Lipid level Acylated ghrelin splice variant (20 µg; 29 amino acids in length (SEQ ID NO:2)) or the Vehicle (1.6% mannitol) was administered once daily for 14 successive days, via the subcutaneous (SC) route, to groups comprising n=10 129Sv male mice. No mortality occurred in any of the animals throughout the entire study period. No clinical signs were observed in any of the animals throughout the entire study period. All animals were subjected to terminal bleeding, under $CO_2$ anesthesia, immediately prior to euthanasia. Terminal blood collection was performed serially as per animal number, and not as per group.
Hematology: Blood samples (at least 100 µl) were collected into pre-labeled EDTA coated tubes. The tubes were pre-labeled and contain the following information:
Study number, group number, animal number and date. The samples were kept until delivery and analysis at 2-8 ° C. Hematology parameters that were tested using Sysmex KX-21™are: WBC, RBC, HGB, HCT, MCV, MCH, MCHC, Platelets. Differential count was preformed manually.
Biochemistry: Blood for biochemistry analysis was collected into non-coated pre-labeled tubes. The tubes were pre-labeled and contained the following information: Study number, group number, animal number and date. Following clotting, the blood from each animal was centrifuged, and the serum was collected into two pre-labeled tubes and submitted for analysis as follows: Serum, 250 µl, was kept at 2-8° C. until analysis. The samples were subjected to the following listed tests using Hitachi 917 system: Creatinine, Total bilirubin, Glucose, Triglycerides, Cholesterol, HDL, LDL, Total protein, Globulin, Albumin, Urea, Potassium, Phosphorus, Calcium, Sodium, Chloride, sGOT, SGPT, ALP.
Urinalysis: Urine was collected into pre-labeled tubes (as above) from all animals (where possible) prior to and/or after euthanasia. For all surviving animals, urine collection was performed serially as per animal number, and not as per group. An attempt was made to attain the maximal amount as possible to perform the tests listed below. Urinalysis is performed using a commercial test stick (Bayer, Multistix® 10SG) applied to urine sample and evaluating the following parameters: glucose, ketone, pH value, leukocytes, blood, density, nitrite, bilirubin, urobilinogen and protein.
Necropsy Procedures and Macroscopic Examination: All animals were subjected to a fully detailed necropsy. For all surviving animals, necropsy was performed serially as per animal number, and not as per group, immediately following the scheduled terminal bleeding. At necropsy, a thorough examination is made and any abnormality or gross pathological changes in tissues and/or organs are observed and recorded.
Organ/Tissue Collection: The organs and tissues listed (Brain, Liver, Kidney, Stomach, Pancreas, Lungs, Spleen, Heart, Epididymal WAT, Retroperitoneal WAT, Interscapular BAT) were excised and weighed wet as soon as possible after excision and removal of the attached fat and other connective tissues. All organs from one animal were collected into one container, pre-labeled with the following information: Study number, group number, animal number and date.
Results: Reduced levels of cholesterol in the acylated ghrelin splice variant and un-acylated ghrelin splice variant treated groups were observed (5% & 6%, respectively; See FIG. 1A). Reduced levels of HDL in the acylated ghrelin splice variant and un-acylated ghrelin splice variant treated groups (5% & 6%, respectively; see FIG. 1B). LDL levels remained unchanged in the acylated ghrelin splice variant and un-acylated ghrelin splice variant treated groups treated groups (See FIG. 1C). Increased levels of triglycerides in the acylated ghrelin splice variant (9%) were observed, while the level of triglycerides in the un-acylated ghrelin splice variant treated group remained unchanged (See FIG. 1D).

Example 3

Treatment of Patients with CHD

Human patients with advanced coronary heart disease suffering from the hypercholesterolemia syndrome are believed to benefit from the present disclosure in terms of reduced atherosclerotic blockage, reduced atherosclerotic plaques and a healthier lipid profile.

Patients will receive subcutaneous administration of 10 µg/kg dose of ghrelin splice variant and placebo. The protocol will start at 08.00 hours after an overnight fast. A 22-gauge catheter will be inserted into an antecubital vein for blood sampling. After an equilibration period of 30 min, ghrelin splice variant (10 µg/kg) or placebo (0.9% saline) will be administered subcutaneously.
Investigational treatment: Ghrelin splice variant will be available in GMP-quality in prepared vials of 10 µg/kg from BACHEM AG, Switzerland or NeoMPS Inc., USA. Placebo consists of normal saline (or the vehicle used to dissolve study substance), which will be provided by a hospital pharmacy. Ghrelin splice variant is dissolved in saline, and a dose of 10 µg/kg ghrelin splice variant will be administered to the patient.
Assessments of efficacy:
(1) Cardiovascular autonomic function: for the screening of autonomic disorders, a 20 minute Holter EKG will be performed, and the SDNN value determined.
(10) Mediators of the proinflammatory reaction (CRP, IL-6, TNF-α), the activated metabolism (free fatty acids, triglycerides, insulin, glucose, leptin), the gut-brain axis (ghrelin), and the somatotrophic axis (IGF-1, free testosterone) will be determined as baseline in the first week. A urine sample will be reserved for assessment of proteolysis-inducing factor (PIF), a mediator of the paraneoplastic anorexia/cachexia syndrome.

Example 4

Treatment of Patients with Obesity

Human patients with obesity are believed to benefit from the present disclosure in terms of reduced weight gain, reduced plasma glucose level and a healthier lipid profile.

Patients will receive a daily subcutaneous administration of 10 μg/kg dose of ghrelin splice variant and placebo. The protocol will start at 08.00 hours after an overnight fast. A 22-gauge catheter will be inserted into an antecubital vein for blood sampling. After an equilibration period of 30 min, ghrelin splice variant (10 μg/kg) or placebo (0.9% saline) will be administered subcutaneously.

Investigational treatment: Ghrelin splice variant will be available in GMP-quality in prepared vials of 10 μg/kg from BACHEM AG, Switzerland or NeoMPS Inc., USA. Placebo consists of normal saline (or the vehicle used to dissolve study substance), which will be provided by a hospital pharmacy. Ghrelin splice variant is dissolved in saline, and a dose of 10 μg/kg ghrelin splice variant will be administered to the patient.

Assessments of efficacy:
(1) Percent change and absolute change in body weight.
(2) Waist circumference, waist-hip ratio, change in BMI, Sagittal diameter and DEXA; blood tests (Triglycerides, Cholesterol-total, LDL-C, HDL-C, LDH, Blood glucose fasting, HbA1c, C-reactive protein, Insulin and Adiponectin); data from questionnaires (Baecke Questionnaire, Satiety & Appetite Questionnaire, POMS, and Impact of Weight on Quality of Life Questionnaire-Lite Version (IWQOL-Lite)).
(3) Changes in HOMA (Homeostasis Model Assessment) index value; Changes in baseline glucose, and post-charge glucose plasma levels. Changes in serum insulin, leptin and adiponectin, inflammatory markers and oxidative stress markers.
(4) Mediators of the proinflammatory reaction (CRP, IL-6, TNF-α), the activated metabolism (free fatty acids, triglycerides, insulin, glucose, leptin), the gut-brain axis (ghrelin), and the somatotrophic axis (IGF-1, free testosterone) will be determined as baseline pretreatment and measured weekly to evaluate the progress of treatment. A urine sample will be reserved for assessment of metabolites.

Example 5

Treatment of Patients with Diabetes

Human patients with Diabetes are believed to benefit from the present disclosure in terms of reduced plasma glucose level and a healthier lipid profile.

Patients will receive a daily subcutaneous administration of 10 μg/kg dose of ghrelin splice variant and placebo. The protocol will start at 08.00 hours after an overnight fast. A 22-gauge catheter will be inserted into an antecubital vein for blood sampling. After an equilibration period of 30 min, ghrelin splice variant (10 μg/kg) or placebo (0.9% saline) will be administered subcutaneously.

Investigational treatment: Ghrelin splice variant will be available in GMP-quality in prepared vials of 10 pg/kg from BACHEM AG, Switzerland or NeoMPS Inc., USA. Placebo consists of normal saline (or the vehicle used to dissolve study substance), which will be provided by a hospital pharmacy. Ghrelin splice variant is dissolved in saline, and a dose of 10 μg/kg ghrelin splice variant will be administered to the patient.

Assessments of efficacy:
(1) Percent change and absolute change in plasma glucose level.
(2) Glucose level control as measured by change from baseline in fasting plasma glucose
(3) Difference in HbAlc levels after 12 weeks, 26 weeks treatment
(4) Self Monitoring of Blood Glucose (SMBG; lipids as measured by change from baseline in total triglycerides, total; cholesterol, LDL cholesterol, and HDL cholesterol; change from baseline in circulating free fatty acids; change from baseline in serum uric acid; change from baseline in serum adiponectin.

I claim:

1. A method of modulating high cholesterol levels comprising administering to a mammal in need thereof a pharmaceutically acceptable amount of:
   (a) ghrelin splice variant;
   (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 90% homology to SEQ ID NO:1; or
   (c) a mixture thereof.

2. The method of claim 1, wherein the compound according to formula Z1-(X1)m-(X2)-(X3)n-Z2 has at least 95% homology to SEQ ID NO:1.

3. The method of claim 1, wherein the compound according to formula Z1-(X1)m-(X2)-(X3)n-Z2 has at least 98% homology to SEQ ID NO:1.

4. The method of claim 1, wherein the ghrelin splice variant of (a) or the ghrelin splice variant-like compound of (b) is 22-29 amino acids in length.

5. The method of claim 1, wherein the bulky hydrophobic group is an acyl group or a fatty acid group.

6. The method of claim 1, wherein (X1)m-(X2) is Gly-Xaa-Ser*, Gly-Xaa-Dpr*, or Gly-Xaa-Cys, wherein * indicates that the amino acid residue is modified with a bulky hydrophobic group and Xaa is any naturally occurring amino acid or synthetic amino acid.

7. The method of claim 6, wherein Xaa is Ser.

8. The method of claim 1, wherein (X3)n comprises a fragment of SEQ ID NO:6.

9. The method of claim 1, wherein the ghrelin splice variant-like compound of (b) has the amino acid sequence set forth in SEQ ID NO:2, SEQ ID NO:3, or SEQ ID NO:4.

10. The method of claim 9, wherein the second or third amino acid of the ghrelin splice variant-like compound of (b) is modified with an octanoyl group.

11. The method of claim 1, wherein the ghrelin splice variant of (a) is SEQ ID NO:1, SEQ ID NO:5, SEQ ID NO:6, SEQ ID NO:7, or a peptide of 15 amino acids or more thereof, further wherein the ghrelin splice variant optionally has at least one post translational modification.

12. The method of claim 1, where the mammal is suffering from a Coronary Heart disease.

13. The method of claim 1, wherein administration of ghrelin splice variant of (a) or ghrelin splice variant-like compound of (b) leads to inhibition of appetite, inhibition of food intake, inhibition of weight gain or weight maintenance, reduced body fat mass, reduced or induced body lean mass, or a combination thereof.

14. The method of claim 13, wherein inhibition of food intake produces food intake at least 1% less as compared to food intake prior to inhibition.

15. The method of claim 13, wherein inhibition of food intake produces calorie intake at least 1% less as compared to calorie intake prior to inhibition.

16. The method of claim 1 comprising, after the administering step, the further step of monitoring the effect of the administration of compounds (a), (b), or (c).

17. The method of claim 1, wherein the mammal is a human.

* * * * *

SEQUENCE LISTING

```
<160> NUMBER OF SEQ ID NOS: 7

<210> SEQ ID NO 1
<211> LENGTH: 94
<212> TYPE: PRT
<213> ORGANISM: Homo sapiens

<400> SEQUENCE: 1

Gly Ser Ser Phe Leu Ser Pro Glu His Gln Arg Val Gln Val Arg Pro
1               5                   10                  15

Pro His Lys Ala Pro His Val Val Pro Ala Leu Pro Leu Ser Asn Gln
            20                  25                  30

Leu Cys Asp Leu Glu Gln Gln Arg His Leu Trp Ala Ser Val Phe Ser
        35                  40                  45

Gln Ser Thr Lys Asp Ser Gly Ser Asp Leu Thr Val Ser Gly Arg Thr
    50                  55                  60
```

```
Trp Gly Leu Arg Val Leu Asn Gln Leu Phe Pro Pro Ser Ser Arg Glu
 65                  70                  75                  80

Arg Ser Arg Arg Ser His Gln Pro Ser Cys Ser Pro Glu Leu
             85                  90

<210> SEQ ID NO 2
<211> LENGTH: 29
<212> TYPE: PRT
<213> ORGANISM: Homo sapiens

<400> SEQUENCE: 2

Gly Ser Ser Phe Leu Ser Pro Glu His Gln Arg Val Gln Val Arg Pro
 1               5                  10                  15

Pro His Lys Ala Pro His Val Val Pro Ala Leu Pro Leu
             20                  25

<210> SEQ ID NO 3
<211> LENGTH: 22
<212> TYPE: PRT
<213> ORGANISM: Homo sapiens

<400> SEQUENCE: 3

Gly Ser Ser Phe Leu Ser Pro Glu His Gln Arg Val Gln Val Arg Pro
 1               5                  10                  15

Pro His Lys Ala Pro His
             20

<210> SEQ ID NO 4
<211> LENGTH: 24
<212> TYPE: PRT
<213> ORGANISM: Homo sapiens

<400> SEQUENCE: 4

Gly Ser Ser Phe Leu Ser Pro Glu His Gln Arg Val Gln Val Arg Pro
 1               5                  10                  15

Pro His Lys Ala Pro His Val Val
             20

<210> SEQ ID NO 5
<211> LENGTH: 91
<212> TYPE: PRT
<213> ORGANISM: Homo sapiens

<400> SEQUENCE: 5

Phe Leu Ser Pro Glu His Gln Arg Val Gln Val Arg Pro Pro His Lys
 1               5                  10                  15

Ala Pro His Val Val Pro Ala Leu Pro Leu Ser Asn Gln Leu Cys Asp
             20                  25                  30

Leu Glu Gln Gln Arg His Leu Trp Ala Ser Val Phe Ser Gln Ser Thr
         35                  40                  45

Lys Asp Ser Gly Ser Asp Leu Thr Val Ser Gly Arg Thr Trp Gly Leu
     50                  55                  60

Arg Val Leu Asn Gln Leu Phe Pro Pro Ser Ser Arg Glu Arg Ser Arg
 65                  70                  75                  80

Arg Ser His Gln Pro Ser Cys Ser Pro Glu Leu
             85                  90

<210> SEQ ID NO 6
<211> LENGTH: 181
<212> TYPE: PRT
<213> ORGANISM: Mus musculus
```

```
<400> SEQUENCE: 6

Gly Ser Ser Phe Leu Ser Pro Glu His Gln Lys Ala Gln Val Ser Gln
1               5                   10                  15

Ser Val Ser Leu Ser Pro His Ile Tyr Pro Asp Leu Cys Val Cys Val
                20                  25                  30

Arg Glu Arg Glu Arg Glu Pro Ser Phe Pro Phe Gln Gln Arg Lys Glu
            35                  40                  45

Ser Lys Lys Pro Pro Ala Lys Leu Gln Pro Arg Ala Leu Glu Gly Trp
    50                  55                  60

Leu His Pro Glu Asp Arg Gly Gln Ala Glu Glu Thr Glu Glu Glu Leu
65                  70                  75                  80

Glu Ile Arg Val Cys Thr Gln Ala Pro Ala Cys Ser Tyr Asn Ser Lys
                85                  90                  95

Gly Val Gly Val Trp Arg Val Ser His Met Leu Ala Phe Gln Ala Thr
                100                 105                 110

Gln Gly Leu Glu Ser Ser Thr Asn Ser Ser Thr Arg Gly Ser Glu Ser
            115                 120                 125

Pro Ser Gln Glu Val Thr Val Ser Arg Val Ala Arg Glu Gln Gln Thr
    130                 135                 140

Cys Ala Gln Lys Thr Lys Gln Ile Glu Gly Ser Gln Glu Pro Gly Ser
145                 150                 155                 160

Thr Asp Gly Tyr Arg Asn Arg Arg Lys Pro Cys Leu Ser Gln Asp Leu
                165                 170                 175

Ser Gly Leu Pro Trp
            180

<210> SEQ ID NO 7
<211> LENGTH: 90
<212> TYPE: PRT
<213> ORGANISM: Rattus norvegicus

<400> SEQUENCE: 7

Gly Ser Ser Phe Leu Ser Pro Glu His Gln Lys Ala Gln Val Ser Leu
1               5                   10                  15

Ser Pro Gln Val Pro His Leu Ser Trp Ser Val Val Cys Ser Phe Pro
                20                  25                  30

Phe Gln Gln Arg Lys Glu Ser Lys Lys Pro Pro Ala Lys Leu Gln Pro
            35                  40                  45

Arg Ala Leu Glu Gly Trp Leu His Pro Glu Asp Arg Gly Gln Ala Glu
    50                  55                  60

Glu Ala Glu Glu Glu Leu Glu Ile Arg Val Gly Pro Arg Ala Pro Ala
65                  70                  75                  80

Tyr Ser Cys Asn Ser Lys Gly Phe Gly Val
                85                  90
```